US007666363B2

(12) United States Patent  
Diamond et al.

(10) Patent No.: US 7,666,363 B2  
(45) Date of Patent: Feb. 23, 2010

(54) REAGENT CARTRIDGE

(75) Inventors: Ronald N. Diamond, Anaheim Hills, CA (US); William A. Stark, Costa Mesa, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 365 days.

(21) Appl. No.: 09/946,194

(22) Filed: Sep. 5, 2001

(65) Prior Publication Data  
US 2003/0044323 A1 Mar. 6, 2003

(51) Int. Cl.  
B01L 9/06 (2006.01)

(52) U.S. Cl. .......................................... 422/104; 422/65

(58) Field of Classification Search ........... 422/99–104, 422/63–65; 436/45, 47  
See application file for complete search history.

(56) References Cited

U.S. PATENT DOCUMENTS

| 3,627,276 A | 12/1971 | Gillford et al. |
| 4,849,177 A | 7/1989 | Jordan ........................ 422/64 |
| 5,075,082 A | 12/1991 | Fechtner |
| 5,186,339 A | 2/1993 | Heissler ....................... 311/74 |
| 5,322,668 A | 6/1994 | Tomasso ..................... 422/104 |
| 5,350,564 A * | 9/1994 | Mazza et al. ................. 422/63 |
| 5,397,542 A | 3/1995 | Nelms et al. ................ 422/104 |
| 5,651,941 A * | 7/1997 | Stark et al. .................. 422/104 |
| 5,968,453 A | 10/1999 | Shugart ....................... 422/102 |
| 5,985,218 A | 11/1999 | Goodale ...................... 422/102 |
| 6,136,270 A * | 10/2000 | Maes et al. ................... 422/64 |
| 6,149,872 A | 11/2000 | Mack et al. ................. 422/102 |
| 6,432,694 B1 | 8/2002 | Malmqvist |

FOREIGN PATENT DOCUMENTS

| CA | 2132813 AA | 4/1995 |
| EP | 0 467301 A2 | 1/1992 |
| EP | 0 651254 A1 | 5/1995 |
| WO | WO 94/14073 | 6/1994 |
| WO | WO 00/31535 | 6/2000 |

OTHER PUBLICATIONS

Supplemental European Search Report for EP 02757592.7.

* cited by examiner

*Primary Examiner*—Lyle A Alexander  
(74) *Attorney, Agent, or Firm*—Foley & Lardner LLP

(57) ABSTRACT

A reagent cartridge for a assay device comprises a frame and at least one reagent container. A reagent cartridge frame comprises a plurality of sidewalls, one of the sidewalls includes at least one detent to engage with a flange on a reagent container, and another sidewall includes at least one notch to engage with a rib on the reagent container. The reagent cartridge frame permits various numbers of reagent containers to be placed in the frame at any position and in any order depending on the assay being performed. The reagent cartridge may also be used with as few as one reagent container.

31 Claims, 3 Drawing Sheets

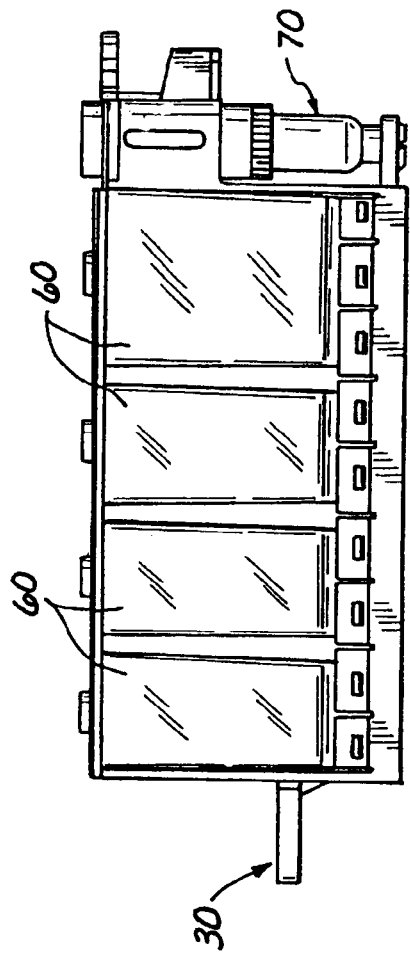
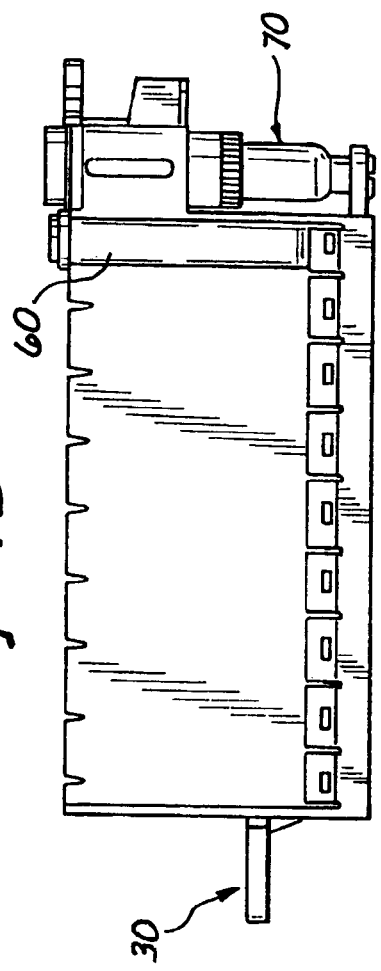
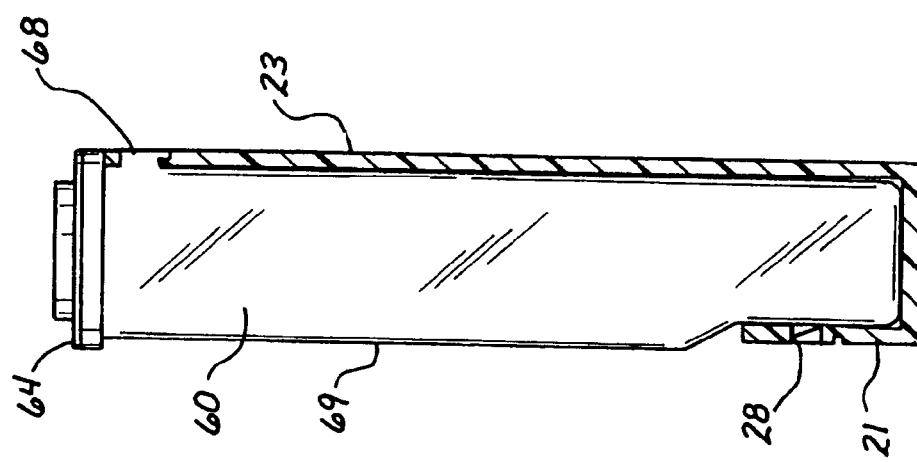

REAGENT CARTRIDGE

SUMMARY OF THE INVENTION

The present invention relates to an apparatus for holding materials or reagents used in automated assay devices. In particular, the invention provides a reagent cartridge for automated assay devices.

In one embodiment of the invention, a reagent cartridge frame comprises a plurality of sidewalls, wherein a first sidewall comprises at least one detent, and a second sidewall comprises a plurality of notches.

In another embodiment of the invention, a reagent cartridge comprises (i) a frame, which comprises a plurality of sidewalls, wherein one sidewall comprises at least one detent, and another sidewall comprises a plurality of notches; and (ii) at least one reagent container, which comprises at least one rib for engagement with one of the notches of the second sidewall, and at least one flange for engagement with one of the detents of the first sidewall.

The notches of the foregoing devices may be positioned at the upper edge of the second sidewall of the reagent cartridge frame. The detents of the first sidewall of the foregoing devices may be positioned in the lower half of the frame.

In certain embodiments of the invention, the sidewalls of the foregoing devices may be substantially parallel to each other. The first sidewall having the detents may be shorter than the second sidewall, thereby maximizing the visibility of the contents of the reagent containers. The second sidewall having the notches may have a continuous solid surface extending the length of the sidewall.

The foregoing reagent cartridge frames may also comprise a handle and/or a particle vial receptacle. In certain embodiments of the invention, the handle is on a third sidewall, and the particle vial receptacle is on a fourth sidewall.

The foregoing devices may comprise a plurality of reagent containers that are positionably interchangeable with each other. The reagent containers may be different sizes. The reagent containers may also have four sides. In one embodiment of the invention, the number of reagent containers equals the number of reagents used in a given assay.

In a particular embodiment of the invention, a reagent cartridge comprises (i) a frame comprising four sidewalls, wherein a first sidewall comprises a plurality of detents positioned in the lower half of the frame, a second sidewall comprises a plurality of notches at the upper edge of the second sidewall, a third sidewall comprises a handle, and a fourth sidewall comprises a particle vial receptacle; (ii) a plurality of reagent containers, wherein the reagent containers comprise a plurality of ribs for engaging with the notches of the second sidewall, and at least one flange for engaging with the detents of the first sidewall; and (iii) a particle vial in a particle vial receptacle of the frame.

In another embodiment of the invention, a reagent cartridge comprises (i) a frame comprising a plurality of sidewalls each having a length; and (ii) a plurality of reagent containers in the frame and positionably interchangeable with each other along the length of the frame, wherein all of the reagent containers are contained within the frame.

In yet another embodiment of the invention, a reagent cartridge for a reagent assay device comprises (i) a frame having a length substantially equal to the length of the reagent cartridge; and (ii) at least one reagent container within the frame, wherein the reagent container is shorter in length than the frame.

In an additional embodiment of the invention, a method for optimizing diagnostic assays comprises providing a reagent cartridge, which comprises a frame and at least one reagent container, wherein the frame is configured to retain different sizes of reagent containers, and the sizes of the reagent containers correspond to the diagnostic assay being performed. The reagent cartridge of the foregoing method may be configured to maximize the number of tests for the diagnostic assay being performed.

Any feature or combination of features described herein are included within the scope of the present invention provided that the features included in any such combination are not mutually inconsistent as will be apparent from the context, this specification, and the knowledge of one of ordinary skill in the art.

Additional advantages and aspects of the present invention are apparent in the following detailed description and claims.

BRIEF DESCRIPTION OF THE FIGURES

FIG. 3 is a sectional view of a reagent cartridge of the invention along line III-III of FIG. 2.

FIG. 4A is a side elevation view of a reagent cartridge of the invention illustrating the flexibility of positioning the reagent containers within the reagent cartridge frame.

FIG. 4B is a side elevation view of a reagent cartridge of the invention illustrating the reagent frame with only one reagent container.

DETAILED DESCRIPTION OF THE INVENTION

Figure 1:
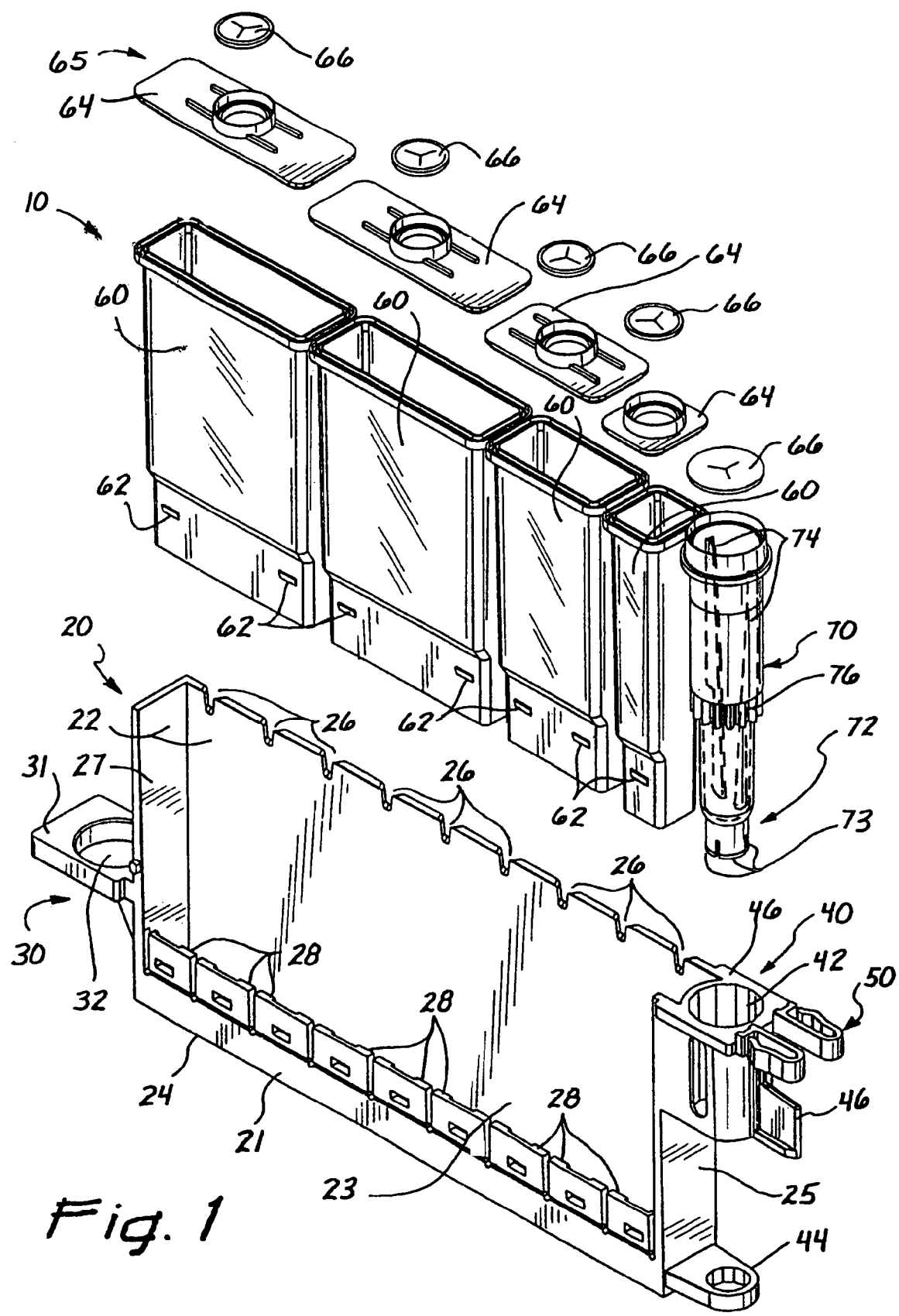
FIG. 1 is an exploded perspective view of a reagent cartridge of the invention.

Referring to the figures, and specifically FIG. 1, reagent cartridge 10 comprises a frame 20 and at least one reagent container 60. A "frame", as used herein, is an apparatus composed of structural elements fitted together, and thereby united to form a monolithic structure. In embodiments where the frame is injection molded from plastic, the frame is a single monolithic structure. Accordingly, frame 20 is an apparatus that holds one or more reagent containers 60 in fixed relationship. A "reagent container", as used herein, is a container that can retain a liquid. Reagent containers may be circular, triangular, or rectangular in cross-section, or a combination thereof. Accordingly, reagent container 60 comprises at least three sidewalls (or one sidewall in the example of a container with a circular cross-section), and a bottom, all connected or integrally formed, to prevent liquid from leaking from the container in it's normal upright position. As described herein, reagent container 60 can be positioned at different positions within frame 20 depending on the assay being performed by a reagent assay device.

Reagent cartridge 10 is a device having one or more reagent containers containing liquid reagents. The reagent cartridge of the invention may be used in assay devices, including automated clinical assay devices. Assay devices are well known in the art, and may be used to perform assays for different reagents. One example of an automated assay device is the Nichols Advantage® System (Nichols Institute Diagnostics (NID), San Juan Capistrano, Calif.). Other automated assay devices are available from companies such as Abbott Laboratories, Beckman Coulter, Inc., and Eastman Kodak Company. The reagent cartridge of the invention permits insertion and removal of multiple reagents contained in individual containers into and out of the assay device. Accordingly, all of the necessary reagents and compositions needed to conduct an assay may be provided in one reagent cartridge.

It is one aspect of the invention disclosed herein to provide a reagent cartridge that permits the number, size, and position of the reagent containers to be varied. For example, one conducting an assay with an assay device can customize the reagent cartridge depending on the assay being performed. For example, an assay may only require one reagent solution to be used to determine whether an analyte is in a sample being measured. Thus, one would want to utilize a single reagent container that can contain a relatively large volume (for example, between 100 and 300 mL) of the reagent solution. Alternatively, an assay may require five different reagent solutions to determine the presence of an analyte within a sample. Thus, one would utilize five different reagent containers to store each of the reagent solutions. Depending on the volume of each solution needed for the assay, reagent containers of different volumes (for example, volumes ranging from about 5 mL to about 50 mL) may be selected to maximize the number of assays performed per reagent cartridge. As another example, for assays in which a particular reagent solution is particularly difficult to obtain or is expensive, a small volume (for example, 3 mL) of that reagent solution may be desired. Thus, providing a reagent cartridge that has a frame configured to retain different numbers and/or sizes of reagent containers is a method for optimizing diagnostic assays. For example, the number of reagent containers can equal the number of reagent solutions required for any given assay.

In addition, one could use a single, small reagent container in the reagent cartridge frame of the invention without the need for additional components, such as additional reagent containers, to effectively lengthen the cartridge to enable the cartridge to fit in an assay device. In other words, the reagent cartridge, and the frame of the reagent cartridge may be substantially equal in length. An example of a reagent cartridge that requires additional reagent containers to lengthen the cartridge and thereby enable the cartridge to fit in an assay device is disclosed in U.S. Pat. No. 6,149,872, entitled "Modular Reagent Cartridge". Thus, even if only one or two reagent solutions are needed in an assay, the device disclosed in U.S. Pat. No. 6,149,872 requires that additional reagent containers (possibly empty reagent containers) be interlockingly added to the frame of the reagent cartridge.

In addition, the positions of the various reagent containers of the reagent cartridge of the invention can be adjusted (e.g., the reagent containers are positionably interchangeable) depending on the settings of the assay device. In other words, if the assay device may be programmed to withdraw a volume of a reagent solution from a particular position of the reagent cartridge, the positions of the reagent containers can be adjusted so that the assay device withdraws the correct solution. Thus, it is one aspect of the invention to provide a reagent cartridge frame that is substantially equal in length to the reagent cartridge and enables the number and position of the reagent containers to be varied without the need for additional components to permit the reagent cartridge to fit in an assay device.

In one embodiment of the invention, as illustrated in FIGS. 1-4, frame 20 comprises a plurality of sidewalls 22, and a bottom surface 24. In a further embodiment of the invention, frame 20 comprises two sidewalls 22. In another embodiment of the invention, frame 20 comprises four sidewalls 22. Referring to the disclosure herein, the terms, "bottom", "top", "lower", "upper", "front", and "rear" refer to the reagent cartridge or reagent cartridge frame as the device is normally positioned in an assay device.

Referring to the embodiment of the invention illustrated in FIG. 1, frame 20 comprises four sidewalls 22, in particular, sidewalls 21 and 23, front wall 25, and rear wall 27; and bottom surface 24. As shown in FIG. 1, sidewall 21 may be shorter in height than sidewall 23. Accordingly, sidewall 21 is configured to maximize the visibility of the reagents stored in the reagent containers. For example, sidewall 21 is sufficiently short to enable one to view a liquid solution within the reagent container, yet sidewall 21 is high enough to securely retain the reagent containers within the frame. Sidewall 21 comprises one or more detents 28. In the embodiment illustrated in FIG. 1, detents 28 are positioned at the upper surface of sidewall 21. In an additional embodiment of the invention, detents 28 are positioned in the lower half of frame 20. Detents 28 are configured to engage with flanges 62 of the reagent cartridges 60, as described herein.

Also as shown in FIG. 1, sidewall 23 comprises one or more notches 26 positioned near the upper edge of sidewall 23. Notches 26 are configured to engage with ribs 68 provided on reagent cartridges 60, as described herein (FIG. 3). Sidewall 23 is illustrated as forming a continuous, flat, solid surface; however, in other embodiments of the invention, sidewall 23 may include one or more apertures or holes therein. Sidewall 23 is configured to receive a label that provides information regarding the assays performed with the reagent cartridge, such as, identification of the contents stored in the reagent containers, the assay being conducted, location of reagent solutions, and/or reagent lot specific information. An example of a label is a bar code label. As one skilled in the art will readily understand, sidewall 23 is configured with sufficient surface area to permit the application of the label, as described above. As illustrated in FIG. 1, sidewall 21 and sidewall 23 are parallel to each other.

In the embodiment of the invention illustrated in FIG. 1, front wall 25 comprises a particle vial receptacle 40 and a flexible latch 50. Particle vial receptacle 40 comprises an aperture 42 extending vertically towards the bottom of frame 20. Aperture 42 is formed by receptacle sidewalls 46. In one embodiment, the cross-section of aperture 42 is circular. Front wall 25 further comprises a particle vial catch 44 configured to receive one end of particle vial 70, described herein.

In the embodiment of the invention illustrated in FIG. 1, rear wall 27 comprises a handle 30 permitting insertion and removal of the reagent cartridge into an assay device. Handle 30 comprises a handle frame 34 surrounding a handle aperture 32. Handle aperture 32 may permit a user to insert a finger and thereby insert or remove the reagent cartridge into or out of the assay device.

Figure 2:
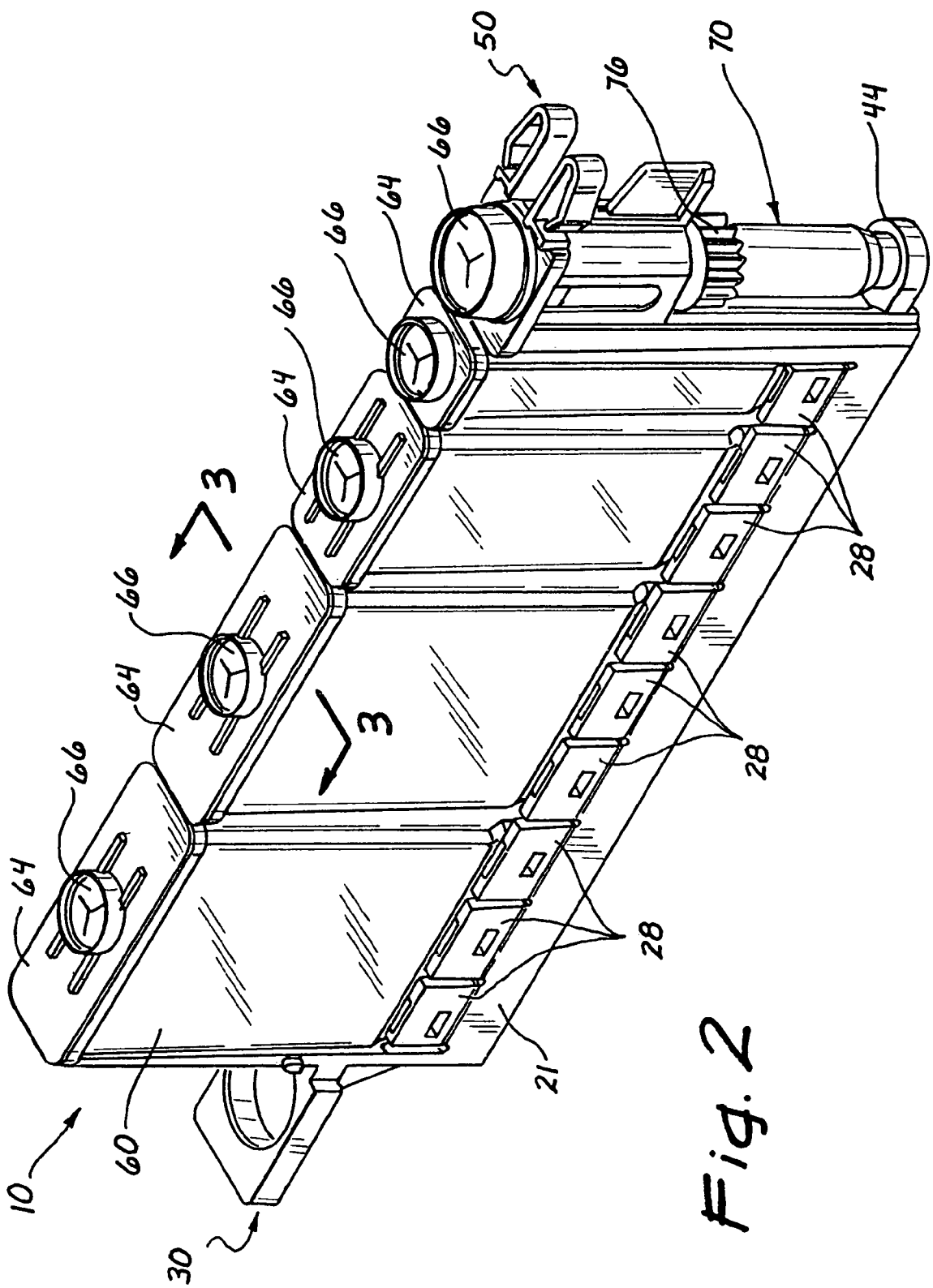
FIG. 2 is a perspective view of a reagent cartridge of the invention.

As indicated herein, frame 20 is configured to hold one or more reagent containers 60. As illustrated in FIG. 1, reagent container 60 comprises a plurality of sidewalls and a bottom plate assembled such that liquid does not leak from the container. In the embodiment illustrated in FIG. 1, reagent container 60 is illustrated with four sidewalls and a bottom plate. Reagent containers 60 may be made from any suitable material that prevents liquid reagents from leaking, and does not react with the liquid reagents. In addition, the reagent containers may be made from material that permits one to see the contents stored therein. In certain embodiments, the reagent containers will be transparent. Thus, because the sidewalls of the reagent cartridge frame are configured to maximize the visibility of the reagents stored in the reagent containers, and because the reagent containers may be transparent, one can readily and accurately view the contents stored therein. Reagent container 60 of the invention further comprises one or more flanges 62. Flange 62 of reagent container 60 engages with detents 28 of sidewall 21 when reagent container 60 is inserted into frame 20 as illustrated in FIG. 2 and FIG. 3.

Thus, the engagement of flange 62 with detent 28 provides a temporary lock of reagent container 60 to frame 20. As will be appreciated by persons skilled in the art, detent 28 is sufficiently flexible to flex outwardly from frame 20 when reagent container 60 is inserted into the frame. As reagent container 60 is lowered into frame 20, detent 28 will flex outwardly from frame 20 until flange 62 is low enough to engage with detent 28. The resilient properties of detent 28 will cause detent 28 to flex inwardly into frame 20 and thereby engage with flange 62.

Reagent container 60 is also configured to receive a cover 65. In the embodiment of the invention illustrated in FIGS. 1-4B, cover 65 comprises lid 64 and seal 66. Seal 66 is configured to permit insertion of a probe or aspirator of an assay device into reagent container 60 while minimizing evaporation effects of the reagent therein. Seal 66 may be fabricated from any suitable material that is non-reactive with the solution within the container, and that permits insertion and removal of the probe of the assay device and still retains an uncontaminated reagent solution. One example of a suitable material for seal 66 is silicone rubber. Seal 66 may be provided with one or more slits to facilitate movement of a probe into and out of the reagent container. Seal 66 is retained in lid 64 by a swaged engagement, for example. Cover 65 may then be positioned on reagent container 60 to enclose the container and prevent contamination of the reagent solution therein.

Reagent container 60 also comprises at least one rib 68 positioned on one of the walls of the reagent container. In the embodiment of the invention illustrated in FIGS. 1-2, two ribs 68 are provided on all but the smallest of the reagent containers. In the embodiment illustrated in FIGS. 1-2, the smallest reagent container has one rib 68. As illustrated in FIG. 3, rib 68 is configured to engage with notch 26 of reagent cartridge frame 20. One skilled in the art will accordingly understand that reagent container 60 is thereby laterally secured within the frame 20 by the engagement of rib 68 with notch 26. Rib 68 is configured to engage with notch 26 in such a manner that facilitates retention of reagent container 60 to frame 20. For example, in one embodiment of the invention, rib 68 is flared outwardly near the portion of the rib that will be adjacent the exterior surface of wall 23. Such a configuration is commonly called a "dovetail" engagement. Thus, when the reagent container is engaged with the reagent cartridge frame, rib 68 is flush with the exterior surface of sidewall 23, but is configured to prevent the reagent container from being pulled away from, or otherwise dislodged from, the inner surface of sidewall 23. In other words, in the embodiment illustrated in the figures, ribs 68 permit reagent containers to be vertically inserted and removed from the reagent cartridge frame, and prevent or reduce the lateral movement of the reagent containers from the frame.

As persons skilled in the art will readily understand, the plurality of notches 26 illustrated in the figures enable the reagent containers to be positioned at various locations within the frame 20. A comparison of FIG. 2 and FIG. 4A indicates that the largest volume reagent container may be positioned closest to the rear wall of the frame (FIG. 2), or may be positioned near the front wall of the frame (FIG. 4A). Similarly, the largest reagent container could be positioned near the middle of the frame if so desired. Furthermore, if only a small volume of one reagent is needed, a single, relatively small reagent container may be provided in the frame (FIG. 4B).

Reagent cartridge 10 also comprises a particle vial 70 to store a liquid suspension of a particulate matter. Particle vial 70 comprises a plug 72, which engages with particle vial catch 44 when the particle vial is inserted into particle vial receptacle 40 of frame 10. As illustrated in FIG. 1, plug 72 is a device that lockingly engages with catch 44 by providing a plurality of flexible tabs 73 that engage with catch 44. Particle vial 70 also comprises one or more fins 74 extending vertically along the interior wall of particle vial 70. In the embodiment illustrated in FIG. 1, two fins 74 are provided. In one embodiment of the invention, two fins 74 are positioned less than 180 degrees from each other. Fins 74 may extend along the entire vertical interior surface of particle vial 70 and may extend along the bottom of particle vial 70. Fins 74 are provided to mix the contents of the liquid solution stored within particle vial 70. As described herein, a gear 76 is provided on the outer surface of particle vial 70. Gear 76 engages with a drive mechanism operatively attached to a motor of the assay device. Gear 76 accordingly causes particle vial 70 to rotate about a vertical axis extending through the center of the cross section of particle vial 70. Fins 74 accordingly will cause currents in the solution contained within particle vial 70. Thus, any particulate matter of the solution will be agitated such that the particulate matter becomes suspended in the solution. In one embodiment of the invention, the particulate matter comprises magnetic particles.

Although detents are illustrated in the lower half of frame 20, in other embodiments of the invention, detents 28 may be provided in the upper half of frame 20 so long as the sidewall to which the detents are attached extends to the upper half of frame 20. As will be appreciated by those skilled in the art, detents positioned in the upper half of frame 20 would engage with flanges 68 provided near the upper portion of reagent containers 60. In yet a further embodiment of the invention, detents 28 may be provided on two opposing sidewalls, such as sidewalls 21 and 23, as illustrated in FIG. 1. In such an embodiment, detents 28 on sidewall 23 permit reagent containers 60 to be fixedly positioned within frame 20 without the use of notches 26, described herein.

Although notches 26 are illustrated as being positioned at the upper edge of sidewall 23 (FIGS. 1, 3, and 4B), in additional embodiments of the invention, notches can be provided lower on sidewall 23. In such embodiments, the notches may provide a groove or channel extending the vertical length from the top of sidewall 23 to the bottom of the notch, or the notches could be enclosed and thereby form an aperture or hole to engage with rib 68. In embodiments of the invention where the notch 26 defines a groove or a channel, the bottom of the notch can be positioned at any location along sidewall 23, for example, the notch could end in the middle of the sidewall, or at the bottom of the sidewall. In embodiments of the invention where the notch is a hole in a sidewall, the rib should extend perpendicularly from the surface of the reagent container to which it is attached. Thus, the reagent container could be slid into the frame, and a flange would engage with detent 28, and a rib would engage with the hole in the sidewall.

As described herein, the components of the reagent cartridge of the invention are preferably made from a non-reactive, leak resistant material, such as plastic. The seals may be made from silicone rubber. Although the components of the reagent cartridge may be formed individually, and subsequently assembled, it is preferable to utilize injection molding methods as is well known in the art.

By way of example, and not by way of limitation, reagent cartridge 10 of the invention may be used in the Nichols Advantage® system in an immunoassay for a protein in a serum sample. In particular, the reagent cartridge frame illustrated and described herein is configured so that the length and width of reagent cartridge 10, and the features 40 and 50 are required for use in the Nichols Advantage® system. In other embodiments of the invention used for other assay devices, the geometry and components of the reagent cartridge can vary.

The reagent cartridge of the aforementioned immunoassay may comprise a particle vial 70 comprising a magnetic particle solution; a first reagent container 60 containing a first antibody solution; a second reagent container 60 containing a second antibody solution; a third reagent container 60 containing an assay buffer solution; and a fourth reagent container 60 containing a wash solution. The particle vial may store approximately 8 mL of liquid, the first and second reagent containers may hold approximately 13 mL of liquid, the third reagent container may hold approximately 30 mL of liquid, and the fourth reagent container may hold approximately 45 mL of liquid.

Particle vial 70 is inserted into particle vial receptacle 40 until plug 72 engages with catch 44. The reagent containers 60 are inserted into frame 20 until detents 28 engage with flanges 62 and ribs 68 engage with notches 26. The reagent containers are positioned based on the settings of the software of the assay device.

The reagent cartridge may then be inserted into a reagent compartment of the assay device until the latch 50 is engaged in the assay device. When the serum samples are placed in the assay device, the assay may begin. An aspirator, such as a pipette, withdraws a predetermined volume of the sample and places it in a well of a cuvette. Another aspirator may, for example, withdraw a predetermined volume of the magnetic particle suspension, which has been agitated as necessary by rotating gear 76 of particle vial 70, the assay buffer solution, and the first antibody solution, and places it in the well of the cuvette containing the sample. In this particular assay, the particle solution is mixed with the other reagents and the resulting solution is added to the well of the cuvette. In other words, the particle solution and the reagents are simultaneously added to the well. In other embodiments, the assay may be designed to permit serial additions of the reagents to the well, for example, the sample may be added to the well, followed by the assay buffer solution and the first antibody solution. After a sufficient amount of time determined by the operators of the assay, the particle solution may be added to the well. The aspirator can be used in multiple reagent containers without contamination due to the resilient seals 66. The aspirator is then washed. After some time, the magnetic particle-antibody complexes are immobilized by a magnetic field, the excess solution is aspirated from the cuvette, and a wash solution is applied to the well of the cuvette.

After washing, the second antibody solution is added to the well of the cuvette. After some time, the magnetic particle/antibody complex is immobilized, the second antibody solution is removed, and the well is washed. The cuvette is transferred to a luminometer, and trigger solutions are then added to the well of the cuvette. A signal is then measured indicating the amount of protein in the sample. Several assays may be performed using the reagent cartridge until the reagent containers are empty. When the reagent containers are empty or when the assays are completed, the reagent cartridge may then be removed from the assay device and a new reagent cartridge can be inserted into the reagent compartment. If the position of the reagent containers needs to be changed, the reagent containers may be removed from the frame by extending the detents on the frame sidewall from the frame to disengage from the flanges on the reagent containers. After the detents are disengaged, the reagent containers may then be removed.

While this invention has been described with respect to various specific examples and embodiments, it is to be understood that the invention is not limited thereto and that it can be variously practiced with the scope of the following claims.

We claim:

1. A reagent cartridge comprising:
  (i) a unitary frame comprising a first sidewall, a substantially opposing second sidewall, a third sidewall contacting the first sidewall and the second sidewall, a fourth sidewall opposing the third sidewall and contacting the first and second sidewall, the four sidewalls forming a single cavity to accommodate one or more reagent containers, the maximum height of the first sidewall being shorter than the maximum height of the second sidewall, and the length of the third sidewall and the length of the fourth sidewall are both individually shorter than the length of the first sidewall or the second sidewall, wherein said second sidewall comprises a plurality of notches open to the top edge of said second side wall; and
  (ii) one or more reagent containers located in the cavity of the frame.

2. The reagent cartridge of claim 1, wherein the first sidewall comprises at least one detent.

3. The reagent cartridge of claim 2, wherein the reagent cartridge comprises a plurality of reagent containers.

4. The reagent cartridge of claim 3, wherein the plurality of reagent containers have different sizes.

5. The reagent cartridge of claim 2, wherein the at least one detent is positioned in the lower half of the reagent cartridge frame.

6. The reagent cartridge of claim 2, wherein at least one of the reagent containers comprises at least one rib for engagement with one of the notches of the second sidewall, and at least one flange for engagement with one of the detents of the first sidewall.

7. The reagent cartridge of claim 1, wherein at least one of the reagent containers has four sides.

8. The reagent cartridge of claim 1, wherein the frame comprises a receptacle having an aperture structured to retain a vial.

9. The reagent cartridge of claim 8, wherein the receptacle is located on the fourth sidewall of the frame.

10. The reagent cartridge of claim 8, further comprising a vial in the receptacle.

11. The reagent cartridge of claim 1, wherein the first sidewall is sufficiently shorter than the second sidewall thereby maximizing the visibility of reagents stored in the reagent containers.

12. The reagent cartridge of claim 1, wherein the frame further comprises a handle.

13. The reagent cartridge of claim 12, wherein the handle is located on the third sidewall.

14. The reagent cartridge of claim 1, wherein said reagent containers are positionally interchangeable.

15. The reagent cartridge of claim 1, wherein said reagent cartridge is rectangular.

16. A reagent cartridge comprising:
  (i) a unitary frame comprising a first sidewall, a substantially opposing second sidewall, a third sidewall contacting the first sidewall and the second sidewall, a fourth sidewall opposing the third sidewall and contacting the first and second sidewall, the four sidewalls forming a compartment to accommodate one or more reagent containers, the height of the first sidewall being shorter than the height of the second sidewall, and the length of the third sidewall and the length of the fourth sidewall are both individually shorter than the length of the first sidewall or the second sidewall, wherein said first sidewall comprises at least one detent; and (ii) one or more reagent containers located in the compartment of the frames wherein said one or more reagent containers comprises a protruding flange capable of engaging an aperture in said at least one detent.

17. The reagent cartridge of claim 16, wherein the second sidewall comprises a plurality of notches.

18. The reagent cartridge of claim 17, wherein the second sidewall comprises an upper edge, and the plurality of notches are located at the upper edge of the second sidewall.

19. The reagent cartridge of claim 17, wherein the at least one detent is positioned in the lower half of the reagent cartridge frame.

20. The reagent cartridge of claim 17, wherein at least one of the reagent containers comprises at least one rib for engagement with one of the notches of the second sidewall.

21. The reagent cartridge of claim 16, wherein the reagent cartridge comprises a plurality of reagent containers.

22. The reagent cartridge of claim 21, wherein the plurality of reagent containers have different sizes.

23. The reagent cartridge of claim 16, wherein at least one of the reagent containers has four sides.

24. The reagent cartridge of claim 16, wherein the frame comprises a receptacle having an aperture structured to retain a vial.

25. The reagent cartridge of claim 24, wherein the receptacle is located on the fourth sidewall of the frame.

26. The reagent cartridge of claim 24, further comprising a vial in the receptacle.

27. The reagent cartridge of claim 16, wherein the first sidewall is sufficiently shorter than the second sidewall thereby maximizing the visibility of reagents stored in the reagent containers.

28. The reagent cartridge of claim 16, wherein the frame further comprises a handle.

29. The reagent cartridge of claim 28, wherein the handle is located on the third sidewall.

30. The reagent cartridge of claim 16, wherein said reagent containers are positionally interchangeable.

31. The reagent cartridge of claim 16, wherein said reagent cartridge is rectangular.

* * * * *